United States Patent
Anderson-Bolden et al.

(10) Patent No.: US 10,010,653 B2
(45) Date of Patent: Jul. 3, 2018

(54) METHODS FOR INCREASING COATING STRENGTH TO IMPROVE SCAFFOLD CRIMPING YIELD

(71) Applicant: Abbott Cardiovascular Systems Inc., Santa Clara, CA (US)

(72) Inventors: Erika Danielle Anderson-Bolden, Fremont, CA (US); Xinmin Xu, Mountain View, CA (US); Ni Ding, San Jose, CA (US); Boyd V. Knott, Menifee, CA (US); Marc Culkin, San Diego, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 168 days.

(21) Appl. No.: 15/016,911

(22) Filed: Feb. 5, 2016

(65) Prior Publication Data
US 2017/0224880 A1    Aug. 10, 2017

(51) Int. Cl.
*A61L 31/10*    (2006.01)
*B05D 3/00*    (2006.01)
*A61L 31/16*    (2006.01)

(52) U.S. Cl.
CPC ............. *A61L 31/10* (2013.01); *A61L 31/16* (2013.01); *B05D 3/007* (2013.01); *A61L 2300/416* (2013.01)

(58) Field of Classification Search
USPC ..................................................... 427/372.2
See application file for complete search history.

(56) References Cited

U.S. PATENT DOCUMENTS

| 7,731,740 | B2* | 6/2010 | LaFont | A61F 2/82 |
| | | | | 264/319 |
| 8,046,897 | B2* | 11/2011 | Wang | A61F 2/958 |
| | | | | 29/505 |
| 8,632,845 | B2 | 1/2014 | Chen et al. | |
| 8,795,761 | B2 | 8/2014 | Bobson et al. | |
| RE45,744 | E * | 10/2015 | Gale | A61L 31/10 |
| 2002/0143382 | A1* | 10/2002 | Hijlkema | B29B 13/02 |
| | | | | 623/1.11 |
| 2003/0083732 | A1 | 5/2003 | Stinson | |
| 2005/0118344 | A1* | 6/2005 | Pacetti | A61F 2/958 |
| | | | | 427/422 |
| 2005/0233062 | A1* | 10/2005 | Hossainy | A61F 2/82 |
| | | | | 427/2.1 |
| 2009/0105800 | A1* | 4/2009 | Sabaria | A61F 2/82 |
| | | | | 623/1.11 |
| 2010/0004735 | A1 | 1/2010 | Yang et al. | |

(Continued)

OTHER PUBLICATIONS

Anderson et al. "Melt Chain Dimensions of Polylactide," Macromolecules 2004, 37, 1857-1862.

(Continued)

*Primary Examiner* — Cachet I Sellman
(74) *Attorney, Agent, or Firm* — Squire Patton Boggs (US) LLP

(57) ABSTRACT

Methods of reducing crimping damage to polymer and drug coating on a scaffold are disclosed. The methods include physically aging a coating including a coating polymer and drug mixture on a scaffold in a manner that takes into account the differing kinetics of aging, that is, the different temperature dependence of the aging rate of the polymer and drug.

13 Claims, 6 Drawing Sheets

(56) References Cited

U.S. PATENT DOCUMENTS

| | | | |
|---|---|---|---|
| 2010/0323093 A1* | 12/2010 | Chen | A61F 2/91 427/2.25 |
| 2011/0066222 A1 | 3/2011 | Wang et al. | |
| 2011/0190871 A1 | 8/2011 | Trollsas et al. | |
| 2011/0260352 A1 | 10/2011 | Tang et al. | |
| 2012/0042501 A1 | 2/2012 | Wang et al. | |
| 2013/0071549 A1 | 3/2013 | Chen et al. | |
| 2013/0255853 A1 | 10/2013 | Wang et al. | |
| 2014/0044860 A1* | 2/2014 | Castro | A61F 2/91 427/2.21 |
| 2014/0114399 A1 | 4/2014 | Hossainy et al. | |
| 2016/0374838 A1* | 12/2016 | Pacetti | A61L 31/06 623/1.38 |

OTHER PUBLICATIONS

Bradshaw et al. "Physical Agining in Polymers and Polymer Composites: An Analysis and Method for Time-Aging Time Superposition," Polymer Engineering and Science, Jan. 1997, vol. 37, No. 1, pp. 31-44.

Cheng, Shiwang et al., "Crazing and strain localization of polycarbonate glass in creep," Polymer, 2013, vol. 54, Issue 13, pp. 3363-3369.

Greer et al. "Apparent reversal of physical aging by electron beam irradiation—further investigations." Polymer, 1998, vol. 39, No. 18, pp. 4205-4210.

Lee, Hau-nan & Ediger, M.D., "Mechanical Rejuvenation in Poly(methyl methacrylate) Glasses? Moleuclar Mobility after Deformation," Macromolecules, 2010, vol. 43, pp. 5863-5873.

Lodge et al. "Self-Concentrations and Effective Glass Transition Temperatures in Polymer Blends," Macromolecules, 2000, vol. 33, pp. 5278-5284.

McHerron, et al. "Apparent reversal of physical ageing in amorphouse glassy polymers by electron beam irradiation," Polymer, 1993, vol. 34, No. 5. pp. 915-924.

Struik, L.C. E., "Physical Aging in Plastics and Other Glassy Materials," Polymer Engineering and Science, 1997, vol. 17, No. 3, pp. 165-173.

Zhao et al. "Two DSC Glass Transitions in Miscible Blends of Polyisoprene/ Poly (4-tert-butylstyrene)" Macromolecules 2009, vol. 42, pp. 6777-6783.

\* cited by examiner

METHODS FOR INCREASING COATING STRENGTH TO IMPROVE SCAFFOLD CRIMPING YIELD

BACKGROUND OF THE INVENTION

Field of the Invention

This invention relates polymeric medical devices, in particular, drug delivery coatings for stents or bioresorbable scaffolds.

Description of the State of the Art

This invention relates to radially expandable endoprostheses that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of a scaffold or scaffolding that includes a pattern or network of interconnecting structural elements or struts, formed from wires, tubes, or sheets of material rolled into a cylindrical shape. This scaffolding gets its name because it possibly physically holds open and, if desired, expands the wall of the passageway. Typically, stents are capable of being compressed or crimped onto a catheter so that they can be delivered to and deployed at a treatment site.

Delivery includes inserting the stent through small lumens using a catheter and transporting it to the treatment site. Deployment includes expanding the stent to a larger diameter once it is at the desired location. Mechanical intervention with stents has reduced the rate of restenosis as compared to balloon angioplasty. Yet, restenosis remains a significant problem. When restenosis does occur in the stented segment, its treatment can be challenging, as clinical options are more limited than for those lesions that were treated solely with a balloon.

Stents are generally made to withstand the structural loads, namely radial compressive forces, imposed on the scaffold as it supports the walls of a vessel. Therefore, a stent must possess adequate radial strength if its function is to support a vessel at an increased diameter. Radial strength, which is the ability of a stent to resist radial compressive forces, relates to a stent's radial yield strength and radial stiffness around a circumferential direction of the stent. A stent's "radial yield strength" or "radial strength" (for purposes of this application) may be understood as the compressive loading or pressure, which if exceeded, creates a yield stress condition resulting in the stent diameter not returning to its unloaded diameter, i.e., there is irrecoverable deformation of the stent.

Some treatments with stents require its presence for only a limited period of time. Once treatment is complete, which may include structural tissue support and/or drug delivery, it may be desirable for the stent to be removed or disappear from the treatment location. One way of having a stent disappear may be by fabricating a stent in whole or in part from materials that erode or disintegrate through exposure to conditions within the body. Stents fabricated from biodegradable, bioabsorbable, bioresorbable, and/or bioerodable materials such as bioabsorbable polymers can be designed to completely erode only after the clinical need for them has ended.

Stents are used not only for mechanical intervention but also as vehicles for providing biological therapy. Biological therapy uses medicated stents to locally administer a therapeutic substance. A medicated stent may be fabricated by coating the surface of either a metallic or polymeric scaffold with a polymeric carrier that includes an active or bioactive agent or drug. Polymeric scaffolds may also serve as a carrier of an active agent or drug. An active agent or drug may also be included on a scaffold without being incorporated into a polymeric carrier.

One challenge with a therapeutic coating on a stent is reducing or preventing damage or defects to the coating during manufacturing and use of the stent. Once formed, on a scaffold or a stent body, a coating is subjected to external forces as well as forces arising from deformation of the scaffold itself. A coating is susceptible to damage or loss of adhesion arising from such forces.

INCORPORATION BY REFERENCE

All publications, patents, and patent applications mentioned in this specification are herein incorporated by reference to the same extent as if each individual publication, patent, or patent application was specifically and individually indicated to be incorporated by reference, and as if each said individual publication, patent, or patent application was fully set forth, including any figures, herein.

SUMMARY OF THE INVENTION

Embodiments of the present invention include a method of fabricating a stent comprising: providing a stent including a scaffold and a coating over the scaffold, wherein the coating comprises a polylactide-based polymer mixed with a drug; thermally treating the stent to physically age the coating at a temperature in a range below a glass transition temperature (Tg) of the polymer and below a Tg of the drug, wherein the temperature is selected to be between a temperature of maximum aging rate of the drug in the range and temperature of maximum aging rate of the polymer in the range; and crimping the stent from a fabricated diameter to a reduced diameter for delivery into a vascular lumen, wherein the thermal treatment reduces crimping and/or deployment damage to the coating. The embodiments include one or any combination of the following aspects: wherein the temperature of maximum aging rate of the drug is greater than the temperature of maximum aging rate of the polymer; wherein the thermal treatment increases a strength and modulus of the coating; wherein the polymer is poly (DL-lactide) (PDLLA) and the drug is everolimus and the temperature is 40±2° C.; wherein the drug and the polymer are phase separated into a polymer-rich phase or domain and a drug-rich phase or domain; wherein the drug-rich phase is dispersed in a continuous polymer-rich phase; and wherein a time of the thermal treatment is 20 to 60 min.

Embodiments of the present invention include a method of fabricating a stent comprising: providing a stent including a scaffold and a coating over the scaffold, wherein the coating comprises a polylactide-based polymer mixed with a drug, and wherein the coating includes drug-rich domains and a polymer-rich phase; thermally treating the coating at a first temperature followed by thermally treating the coating at a second temperature different the first temperature, wherein the first temperature is less than a glass transition temperature (Tg) for the drug, the second temperature is less than the glass transition temperatures (Tg's) for the drug and for the polymer and the first temperature is greater than the second temperature, wherein an aging rate of the drug at the first temperature is greater than at the second temperature and the aging rate of the polymer at the second temperature is greater than the aging rate of the polymer at the first temperature; and crimping the stent after the thermal treatments from a fabricated diameter to a reduced diameter for delivery into a vascular lumen, wherein the thermal treatments reduce crimping and/or deployment damage to the coating. The embodiments include one or any combination of the following aspects: wherein the thermal treatments increase a strength and modulus of the coating; wherein the polymer is poly(DL-lactide) and the second temperature is 30 to 35° C.; wherein a time of the thermal treatment at the second temperature is 10 to 15 min; wherein the drug is everolimus or sirolimus and the first temperature 40 to 50° C.; wherein a time of the thermal treatment at the second temperature is 20 to 30 min.

Embodiments of the present invention include a method of fabricating a stent comprising: providing a stent including a scaffold and a coating over the scaffold, wherein the coating comprises a polylactide-based polymer mixed with a drug; thermally treating the coating at a temperature that varies during a thermal treatment time, wherein the temperature starts at a first temperature and decreases to a second temperature during the thermal treatment, wherein the first temperature is less than glass transition temperature (Tg) for the drug, the second temperature is less than the glass transition temperature (Tg) for the drug and for the polymer, wherein an aging rate of the drug at the first temperature is greater than at the second temperature and the aging rate of the polymer at the second temperature is greater than the aging rate of the polymer at the first temperature; and crimping the stent after the thermal treatments from a fabricated diameter to a reduced diameter for delivery into a vascular lumen, wherein the thermal treatments reduce crimping damage to the coating. wherein the temperature decreases linearly between the first temperature and the second temperature; wherein the thermal treatment is performed in a single oven and the temperature within the oven decreases between the first temperature to the second temperature during the treatment time; wherein the thermal treatment increase a strength and modulus of the coating; wherein the polymer is poly(DL-lactide) and the second temperature is 30 to 35° C.; wherein the drug is everolimus or sirolimus and the first temperature 40 to 50° C.; and wherein a time of the thermal treatment is 20 to 60 min.

DETAILED DESCRIPTION OF THE INVENTION

The present invention relates to processes for reducing coating defects of therapeutic coatings on stents or scaffolds caused by crimping the stent over a delivery catheter. In particular, the stent body is a scaffold composed of a metal or bioabsorbable polymer and the therapeutic coating includes biostable or bioabsorbable polymer carrier and a drug. The processes include physical aging of the coating by thermal treating the stent with the coating prior to crimping the stent on the delivery catheter.

In general, a radially expandable stent can have virtually any structural pattern that is compatible with a bodily lumen in which it is implanted. In certain aspects, a stent is composed of a pattern or network of circumferential rings and longitudinally extending interconnecting structural elements of struts or bar arms. In general, the struts are arranged in patterns, which are designed to contact the lumen walls of a vessel and to maintain vascular patency.

Figure 1:
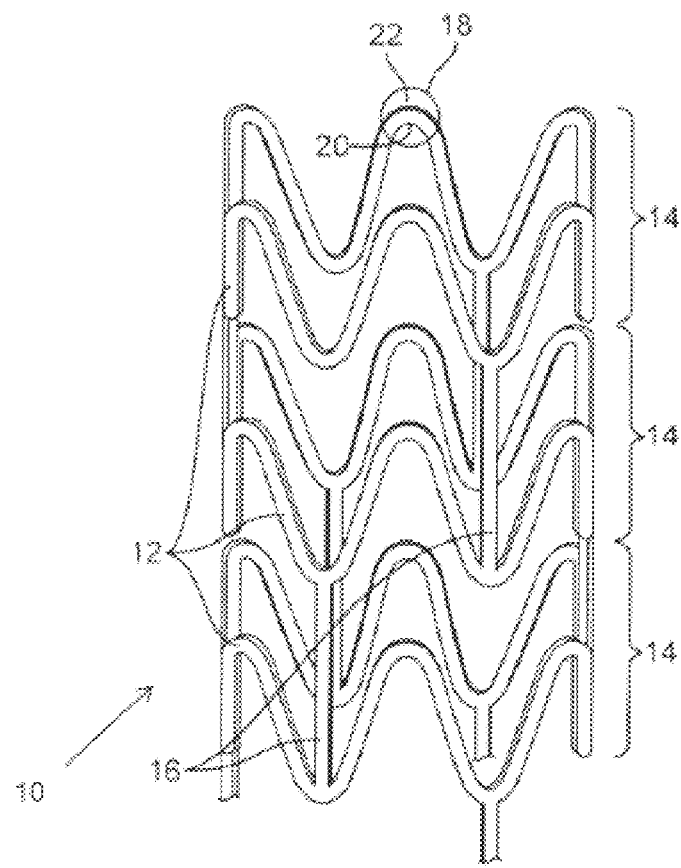
FIG. 1 depicts an exemplary scaffold.

An exemplary structure of a stent body or scaffold is shown in FIG. 1. FIG. 1 depicts a stent 10 which is made up of struts 12. Stent 10 has interconnected cylindrical rings 14 composed of undulating struts. Cylindrical rings 14 are connected by linking struts or links 16. The embodiments disclosed herein are not limited to fabricating stents or to the stent pattern illustrated in FIG. 1. The embodiments are easily applicable to other stent patterns and other devices. The variations in the structure of patterns are virtually unlimited. The outer diameter of a fabricated stent (prior to crimping and deployment) may be between 0.2-5.0 mm. For coronary applications, a fabricated stent diameter is 2.5-5 mm. The length of the stents may be between about 6-30 mm or more depending on the application.

A stent body or scaffold can be made of a polymer or a metal. Metallic materials include stainless steel, cobalt chromium alloys, and nickel titanium alloys. Polymers can be biostable, bioabsorbable, biodegradable, bioresorbable, or bioerodable. Biostable refers to polymers that are not biodegradable. The terms biodegradable, bioabsorbable, bioresorbable, and bioerodable, as well as degraded, eroded, resorbed, and absorbed, are used interchangeably and refer to polymers that are capable of being completely eroded or absorbed when exposed to bodily fluids such as blood and can be gradually resorbed, absorbed, and/or eliminated by the body. A polymer coating on the surface of a stent body or scaffold may also include a biodegradable polymer which may be a carrier for an active agent or drug.

A radial thickness or thickness of the stent body or scaffold may be 80 to 100 microns, 90 to 110 microns, 100 to 120 microns, 120 to 140 microns, 140 to 160 microns, or greater than 160 microns.

The coating is typically much thinner than the struts of the scaffolding, for example, the coating can be 1 to 10 microns, 1 to 3 microns, 3 to 5 microns, or 5 to 10 microns. In general, it is desirable for the radial thickness to be as low as possible. The coating can be conformal, i.e., covers the abluminal, luminal, and sidewall surfaces of the scaffolding or the coating can cover only the abluminal surfaces of the scaffolding.

Figure 2:
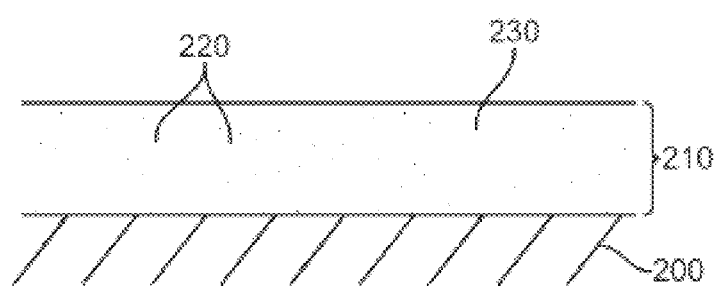
FIG. 2 depicts a cross-section of a stent surface with a polymer and drug layer.

FIG. 2 depicts a cross-section of a stent surface with a polymer and drug coating layer 210 over a substrate 200. Coating layer 210 includes a drug 220 dispersed in a coating polymer 230. A substrate or scaffold can be metallic, polymeric, ceramic, or other suitable material.

A coating is typically formed on a scaffold when at a diameter larger than that required for delivery into vessel. After coating, the coated scaffold may be reduced in diameter or crimped to a diameter suitable for delivery over a support such as a delivery balloon. The crimped scaffold may then be subjected to a sterilization process such as e-beam radiation. The stent is implanted in a patient by positioning the crimped scaffold at a site of stenosis in a blood vessel and expanding the stent with the delivery balloon.

The polymer for a polymer carrier of a therapeutic coating over the scaffold may include poly(L-lactide) (PLLA), poly (DL-lactide) (PDLLA), polyglycolide, poly(L-lactide-co-glycolide), polycaprolactone, or poly(L-lactide-co-caprolactone). A drug may be mixed or dispersed throughout the polymer carrier. The drug may be 20 to 80 wt % of the therapeutic layer, or more narrowly, 30 to 70 wt %, 40 to 60 wt %, 45 to 55 wt %, or 50% of the therapeutic layer. The polymer may further include blends with or copolymers of polylactide and polydioxanone, polyethylene oxide, polyethylene glycol, poly(butylene succinate), poly(trimethylene carbonate), poly(butylene succinate), or any combination thereof. Exemplary drugs include rapamycin, everolimus, novolimus, zotarolimus, or biolimus.

A scaffold retention or crimping process is a critical step to ensure that the scaffold will not be dislodged from the balloon delivery catheter during the clinical use. One type of crimping process typically used for bioabsorbable scaffolds utilizes polymer film to wrap around the drug coated scaffold to reduce the crimping damage to the coating. While coating damage is reduced, the polymer film crimping process can cause strut overlapping during a crimping process, resulting in lower manufacturing yield.

The inventors, however, have observed coating damage when crimping a coated scaffold directly in the crimper without the use of a film. The coating was 50 wt % PDLLA and 50 wt % everolimus. Coating damage or defects were observed on the outer surface of crimped stent. The coating defects that were observed included lifted coating, peeling and voids.

In general, a stent or scaffold and the coating are subjected to stress/strain in localized regions when the stent is crimped and deployed. The inside or concave regions 20, illustrated in FIG. 1, of the bends in the stent pattern or crowns 18 are subjected to high compressive stress and strain when the stent is crimped, but the outside or convex regions 22 of the crowns 18 are subjected to high compressive stress and strain when the stent is deployed. Thus, the coating is susceptible to damage due to deformation of the crowns at the sidewalls, inner surfaces, and outer surfaces of the crowns.

A coating is especially susceptible to damage arising from external forces applied to crimp the scaffold. Generally, stent crimping is the act of affixing the stent to the delivery catheter or delivery balloon so that it remains affixed to the catheter or balloon until the physician desires to deliver the stent at the treatment site. Stent crimping typically involves disposing a stent within an aperture of a crimping device. A force is applied normally to the outer surface of the stent by the walls of the aperture to reduce its diameter to a delivery diameter over the catheter or balloon. For example, in a sliding wedge or iris crimper, adjacent pie-piece-shaped sections move inward and twist, much like the leaves in a camera aperture. The sliding wedges impart primarily normal forces, however, as the wedges slide over each other, they impart some tangential force.

Figure 3:
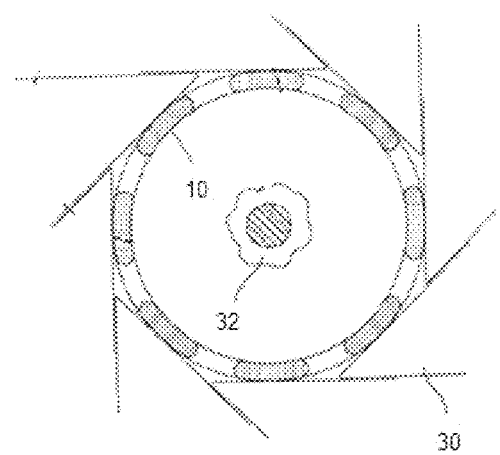
FIG. 3 shows a cross-sectional view of blades of an iris-type crimper taken along the crimper axis when reducing a polymer scaffold diameter from a first, large diameter to a second, smaller diameter.

FIG. 3 is a cross-sectional view of a crimper head and scaffold within the aperture of the crimper head showing the orientation of the blades relative to the scaffold when the aperture forms a first diameter and second, smaller diameter, respectively. The scaffold body 10 is disposed between the blades 30. The scaffold 10 is supported on the collapsed balloon 32 of the catheter when it is placed in the crimper head. Then, as the blade edges engage the scaffold, the scaffold is lifted off the balloon as shown.

An outer surface of a stent such as a polymer coating is susceptible to damage from the surface of the crimping device applied to the outer surface of the stent. Crimper blades are typically metallic so that metallic blade edges are applying force to a polymer surface of a scaffold or polymer surface of a polymer coating. A softer polymer surface is particularly susceptible to damage from a harder metallic surface. The polymer films mentioned above may be disposed between the blade edge and the stent surface to reduce potential damage.

Several types of damage to a polymer coating can occur from forces arising from manufacturing and use of a stent. These include flaps, tears, bare spots, and peeling. The degree of damage may be characterized by the amount of surface area of the stent having damage or compromised surface area. The amount of surface area may be expressed as the percent of surface area of the stent or portion of a stent, such as the percent of the outer surface of a stent or the percent of the width or length of a strut. For example, minor damage may be assigned to be a peel/tear/void with an area of less than a certain amount and major damage above this amount.

The present invention involves increasing coating strength to reduce coating damage during crimping without necessarily changing coating formulation, a coating process, and/or drug release profile. This is achieved by rapid physical aging of the coating after the solution coating process. Physical aging can be viewed as the energetic evolution of a solidified super-cooled liquid or glass below its glass transition temperature (Tg), leading to an increase in strength and modulus of the material over time. Physical aging of a glass can be performed by a heat or thermal treatment. The present invention significantly reduces such coating damage from crimping which makes feasible direct crimping by crimper blades on a polymer coating. The inventors have found that heat treatment of coated scaffolds reduces the coating damage during crimping.

A challenge in developing a process to reduce coating damage of coated scaffold is integrating the process into an overall manufacturing process, as described above. The manufacturing process imposes constraints on individual steps, in particular, time constraints. Specifically, the time for an additional process may be limited. As discussed below, physical aging is a temperature and time dependent process. The present invention addresses the time constraints by reducing the time to perform the physical aging or thermal treatment process which facilitates integration of the thermal treatment process into an overall manufacturing process.

There may also be a constraints or limitations on the magnitude of the aging temperature. Specifically, the temperature of a thermal treatment process may have an upper limit to avoid damage to the drug or to avoid modifications to the scaffold. Undesired modifications to the scaffold may include changes in crystallinity of the scaffold polymer and loss of induced orientation of the scaffold polymer.

Physical aging is a thermodynamic phenomenon that occurs for many materials in a glassy state which is when they are below their glass transition temperature (Tg). Physical aging of a material such as a polymer refers specifically to changes in transient physical and thermodynamic properties of the polymer with time. Physical aging is a typical physical phenomenon of materials of the glass state and all glasses, irrespective of their chemical nature and their being polymeric or monomeric. Physical aging is of particular relevance for amorphous or semi-crystalline polymers that include amorphous domains that have glass transition temperatures (Tg) above ambient temperatures, for example, from about 15° C. to about 35° C., or more narrowly, 20° C. to about 30° C., 25° C., or about 30° C.

When a portion, such as a coating or scaffold, of a device is formed of a material, such as a polymer, the material is typically not at thermodynamic equilibrium. When glassy materials at temperatures below their Tg are not in thermodynamic equilibrium, thermodynamic properties, such as specific volume, enthalpy and entropy are greater than their equilibrium values so they decrease towards their equilibrium values. This process is referred to as physical aging. Physical properties also change as the material ages. For example, during physical aging, physical property changes include an increase in density, increase in modulus, decrease in compliance, increase in stiffness, and a decrease in ultimate strength. The difference between the value of a property not a thermodynamic equilibrium and the value at equilibrium is referred to as an excess property.

The physical aging process is also associated with enthalpy relaxation (a decrease in enthalpy) and can be characterized with differential scanning calorimetry (DSC) by which measures the excess endothermic relaxation peak (excess enthalpy) that occurs near Tg. Therefore, one can measure the extent of the physical aging by characterizing the excess enthalpy using DSC. Excess enthalpy is analyzed from the extra peak area above the base thermogram of a non-aged (or second heating in the DSC testing) sample near glass transition temperature.

A significant feature of physical aging is that the kinetics or the rate of aging, and thus the rate of change of properties, is strongly dependent on aging temperature. In addition, the temperature dependence of the aging rate is different for different materials. In general, the kinetics of the aging process is higher at temperature above ambient, so that the aging process can be accelerated by heat treatment of glassy materials.

Many polymers used as coatings have Tg's above ambient temperatures so that they are glasses at ambient temperatures. Thus, physical aging, such as a by a thermal treatment, can be used to increase strength, stiffness, hardness of the coating which may reduce coating damage. A challenge for the thermal treatment is to determine aging temperature and time that that result in changes in properties that sufficiently reduce coating damage and the aging time that can be integrated into a manufacturing process. An aging time suitable for integration may be 1 min to 60 min, 5 to 30 min, 10 to 30 min, or 20 to 30 min, 30 to 60 min.

Another challenge the inventors have recognized is that for a therapeutic coating, a physical aging process must take into account both the drug and the polymer. The properties of the drug contribute to physical properties of the coating and thus the resistance to coating damage. Many drugs may be glasses at ambient conditions and also be subject to physical aging so that the physical properties are transient as well.

Many polymer and drug mixtures are immiscible systems and form an immiscible system, where the drug and the polymer are phase separated into a polymer-rich phase or domain and a drug-rich phase or domain. The effect of physical aging could be different in these two characteristic domains. The characteristic morphology of the phase-separated mixture will depend on several factors including the relative composition of drug and polymer, the mutual miscibility, and the manner of mixture formation, e.g., solution processing parameters including type of solvent. A challenge in developing an aging process is that the temperature dependence of rate of aging of the drug and polymer will be different. An aging temperature that provides the most rapid aging for the drug will be different than the temperature that provides the most rapid aging for polymer.

A polymer and drug mixture may have a morphology in which the drug is in a dispersed phase and the polymer in a continuous phase. In particular, the inventors have found that a 50/50 mixture of PDLLA and everolimus forms drug-rich dispersed domains in a continuous PDLLA phase. The drug-rich domains are particles that are in the submicron range on average. The PDLLA is an amorphous polymer with a Tg about 52° C. and the everolimus used is an amorphous powder, with a Tg of approximately 86° C.

As indicated, the temperature dependence of the aging rate for the polymer and drug may differ. In particular, in a certain temperature range, the aging rate of the polymer may be higher at a first temperature range than a second temperature range, while the drug may have a higher aging rate in the second temperature range than the first temperature range. For example, the aging rate of the drug may be higher and the polymer lower at a higher temperature range while the polymer may have a higher and the drug lower at a lower temperature range.

Embodiments of the present invention include physically aging a coating including a coating polymer and drug mixture on a scaffold in a manner that takes into account the differing kinetics of aging, that is, the different temperature dependence of the aging rate of the polymer and drug. The physical aging is performed by thermal treatment of the coating. The differing kinetics is taken into account through the selection of aging temperature or temperatures which take advantage of the temperature ranges of higher aging rates of both the polymer and the drug.

Each of these embodiments includes providing a stent including a stent body and a coating over the stent. The coating includes a bioabsorbable polymer mixed with a drug. The bioabsorbable polymer may be a polylactide-based polymer such as PDLLA. The polymer may be a completely amorphous polymer or a semicrystalline polymer with amorphous domains. The Tg of the polymer is greater than ambient temperature, or more narrowly, at least 40° C., at least 50° C., or at least 60° C. The Tg of the drug is greater than ambient temperature, or more narrowly, at least 40° C., at least 50° C., at least 60° C., at least 70° C., or at least 80° C. The temperature of maximum aging rate of the drug may be greater than the temperature of maximum aging rate of the polymer.

The coating may be 10 to 90 wt % drug, or more narrowly, 20 to 80 wt %, 30 to 70 wt %, or 40 to 60 wt %, or 50 wt % drug. The coating may be a phase-separated mixture including a drug-rich domain and a polymer rich domain, as described above.

Thermal treatment may refer to heating a coating or exposing a coating to a temperature greater than ambient. The thermal treatment temperature or temperatures may refer to the temperature that the stent or coating is exposed to or temperature of the coating, or both.

Various methods may be used for thermal treatment of the coating. These include, but are not limited to, vacuum oven, convection oven, conductive heating (e.g., heating element adjacent to stent or coating), or blowing warm inert gas on the coating.

In a first embodiment, the method further includes thermally treating the stent to physically age the coating at a temperature in a range below a glass transition temperature (Tg) of the polymer and below a Tg of the drug. The thermal treatment temperature may be greater than ambient temperature, for example, greater than 30° C. The temperature may be selected to be between a temperature of maximum aging rate of the drug in the range and maximum aging rate of the polymer in the range. The aging rate may correspond to the rate of change of excess enthalpy as measured by differential scanning calorimetry (DSC). The method then includes crimping the stent from a fabricated diameter to a reduced diameter for delivery into a vascular lumen. The thermal treatment may reduce crimping damage to the coating.

In some embodiments, thermal treatment temperature is limited by two factors: (1) the thermal treatment temperature should be below a temperature that the drug degrades and (2) the temperature should be below a temperature that the coating begins to flow.

Since the temperature of maximum aging rates of the polymer and drug are different, there may be several ways of choosing a thermal processing temperature to accelerate or optimize the aging rate of polymer and drug-rich phases. In one aspect, the thermal processing temperature may be half way or approximately half way between the respective temperatures of maximum aging rate. In another aspect, the thermal treatment temperature may be closer to the slower aging component. In other aspects, the relative composition of drug and polymer in the coating may influence the selection. The treatment temperature may be selected to be closer to the major component.

Figure 4:
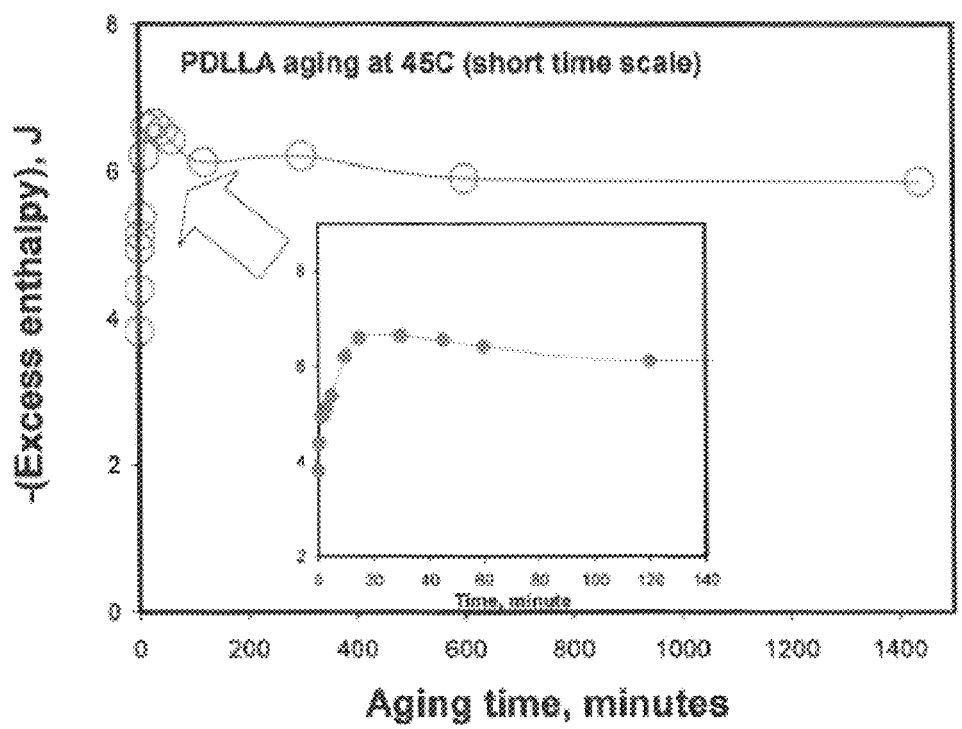
FIG. 4 shows the excess enthalpy versus aging time of pure PDLLA of resin samples aged at 45° C.
Figure 5:
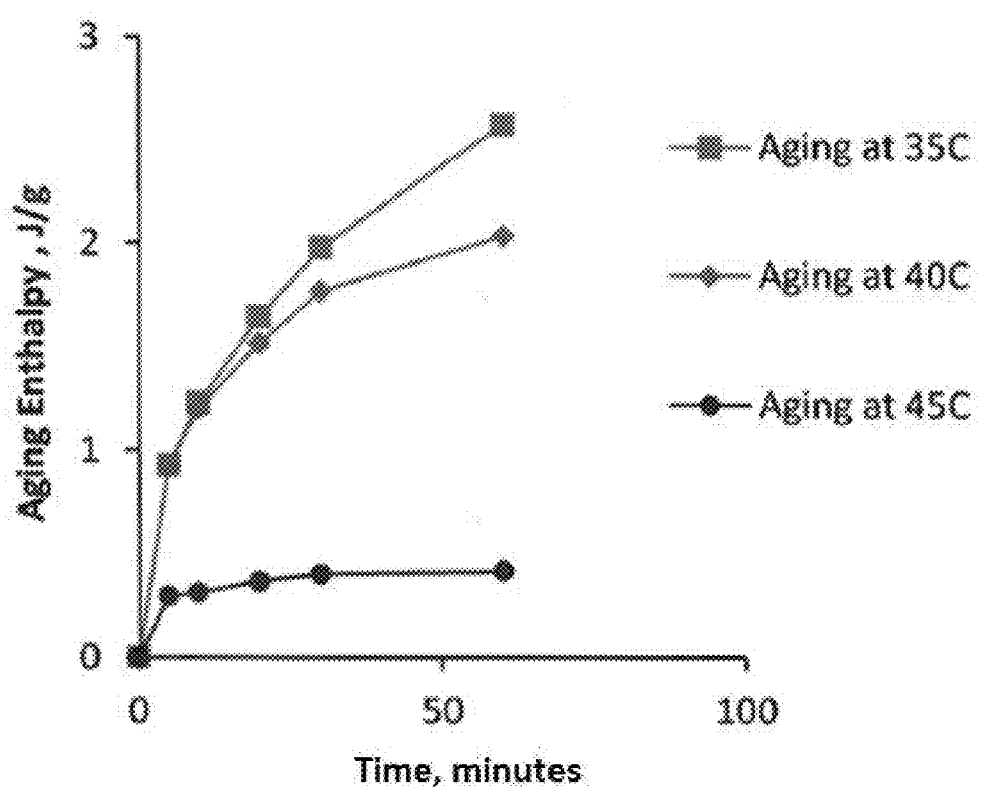
FIG. 5 shows the excess aging enthalpy (normalized) versus aging time of PDLLA in a PDLLA/everolimus coating on a metal stent for aging temperatures of 35, 40, and 45° C.
Figure 6:
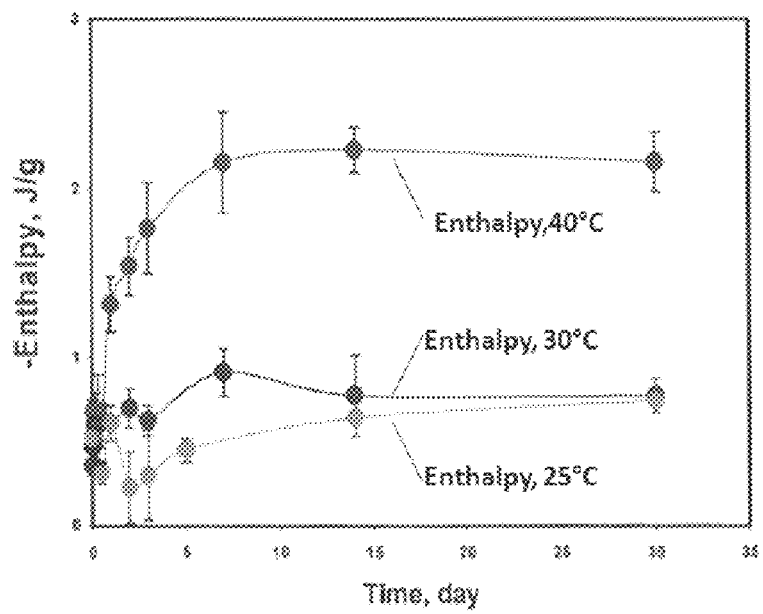
FIG. 6 shows the aging enthalpy versus aging time for everolimus in a PDLLA/everolimus coating on a metal stent at aging temperatures of 25, 30 and 40° C.

DSC experiments of a 50/50 PDLLA/everolimus coating shown in FIGS. 4 to 6 indicate that the aging rate of PDLLA is higher at lower temperature, about 35° C., and everolimus has a faster aging rate at higher temperatures, about 45° C. Therefore, the thermal treatment temperature may be selected to be between these two temperatures. In certain aspects, the thermal treatment temperature for a PDLLA/everolimus coating may be selected to be 35 to 45° C., 35 to 40° C., 40 to 45° C., 40° C., 40±2° C., or 40±3° C.

The thermal treatment time may be 10 to 60 min, 10 to 15 min, 10 to 20 min, 15 to 25 min, 20 to 30 min 20 to 25 min, 30 to 60 min, 40 to 60 min, or greater than 60 min. The treatment time may be adjusted to obtain a selected change or value of coating mechanical properties, for example, strength, modulus, or hardness. The treatment time may also be adjusted to obtain a desired reduction in damage or degree of damage caused by crimping. The degree of damage in terms of percent peels and tears of a thermally treated crimped scaffold is less than 5%, less than 3%, 1 to 3%, or 1 to 5%.

In a second embodiment, a thermal treatment of the coating can include more than one stage or step of thermal treatment. For a two stage process, one stage may be for rapidly aging the drug-rich phase and a second phase may be for rapidly aging the polymer-rich phase. The thermal treatment temperature for a stage may be selected to for rapidly age one of the phases, the drug-rich or the polymer-rich phase. The method may include thermally treating the coating at a first temperature followed by thermally treating the coating at a second temperature different from the first temperature. The first temperature is less than a glass transition temperature (Tg) for the drug, the second temperature is less than the glass transition temperatures (Tg's) for the drug and for the polymer. The first temperature can be below, equal to, or greater than the polymer Tg. The first temperature may be greater than the second temperature or, alternatively, the first temperature may be less than the second temperature. The physical aging reversal must be taken into account, e.g., if the temperature is too close to the Tg of the component with the lower Tg.

In one aspect, the aging rate of the drug at a higher temperature is greater than at a lower temperature and the aging rate of the polymer at the lower temperature is greater than the aging rate of the polymer at the higher temperature. Thus, the drug-rich phase may be rapidly aged at the higher temperature and the polymer-rich phase may be rapidly aged at the lower temperature. The inventors have found this aspect to be the case for the PDLLA/everolimus coating.

In another aspect, the aging rate of the drug at a lower temperature is greater than at a higher temperature and the aging rate of the polymer at the higher temperature is greater than the aging rate of the polymer at the lower temperature. Thus, the drug-rich phase may be rapidly aged at the lower temperature and the polymer-rich phase may be rapidly aged at the higher temperature.

For either of these aspects, the coating may be first thermally treated at the higher temperature, followed by thermal treatment at the lower temperature.

Alternatively for either aspect, the coating may be first thermally treated at lower temperature, followed by thermal treatment at the higher temperature.

The thermal treatment time for a stage may be 10 to 60 min, 10 to 15 min, 10 to 20 min, 15 to 25 min, 20 to 30 min 20 to 25 min, 30 to 60 min, 40 to 60 min, or greater than 60 min. The thermal treatment time for each stage may be the same or may be adjusted according to the aging rates of the polymer and drug. For example, the aging rate of the drug-rich phase during its rapid aging stage may be slower than the polymer-rich phase in its rapid aging stage. In this case, the treatment time of the drug-rich rapid aging stage may be longer than the polymer-rich rapid aging stage.

The treatment time may be adjusted to obtain a selected change or value of coating mechanical properties, for example, strength, modulus, or hardness. The treatment time may also be adjusted to obtain a desired reduction in damage or degree of damage that results from the crimping.

In one aspect, the two stage thermal treatment process may be performed using a single oven. In this aspect, the coated scaffold may be disposed within the oven and treated at a temperature of the first stage followed by treating the coated scaffold at the temperature of the second stage. Alternatively, a two stage treatment process may be performed using two separate ovens. A coated scaffold is treated at the first stage temperature in a first oven and then treated at the second stage temperature in a second oven.

For a PDLLA/everolimus coating, a temperature of the stage for rapidly aging the drug phase or domain may be 45° C., 45 to 50° C., or 43 to 47° C. A temperature of the stage for rapidly aging the polymer-rich phase may be 35° C., 35 to 40° C., or 33 to 37° C. The treatment time for the drug-rich rapid aging stage may be longer than the polymer-rich rapid aging stage due to the slow aging rate of the drug-rich phase. The treatment time for the drug-rich phase rapid aging stage may be 20 to 40 min, 20 to 60 min, 50 to 60 min, 20 to 30 min, 20 to 25 min, 25 to 30 min, or 25 min. The treatment time for the polymer-rich phase rapid aging stage may be 10 to 30 min, 10 to 20 min, 20 to 30 min, 10 to 15 min, 15 to 20 min, or 15 min.

In a third embodiment, the method includes thermally treating the coating at a temperature that varies during a thermal treatment time. In one aspect, the temperature starts at a first temperature and decreases or increases to a second temperature during the thermal treatment. The increase or decrease in temperature from the first to the second temperature may be monotonic. The first and second temperatures are less than glass transition temperatures (Tg's) of the drug and the polymer.

The first temperature may correspond to a temperature for rapidly aging the drug rich phase and the second temperature may correspond to a temperature for rapidly aging the polymer rich phase. Alternatively, the first temperature may correspond to a temperature for rapidly aging the polymer-rich phase and the second temperature may correspond to a temperature for rapidly aging the drug-rich phase.

In this third embodiment, the temperature may be decreased or increased linearly between the first temperature and the second temperature. Alternatively, the temperature may be decreased or increased nonlinearly between the first temperature and the second temperature.

A nonlinear temperature change with time may be used when one of the phases has a slower aging rate than the other phase. For example, when the temperature is increased or decreased from the rapid aging temperature of the drug rich phase, the slope of time versus temperature may be relatively low initially and gradually increase with time. As a result, the coating is exposed to a temperature range that rapidly ages the drug-rich phase for a longer period of time.

In one aspect, temperature of rapid aging of the drug rich phase is higher than the temperature of rapid aging of the polymer-rich phase. The temperature is decreased at a slower rate initially followed by a faster rate of decrease to the temperature of rapid aging of the polymer-rich phase. For example, the slower rate may be 0.05 to 0.2° C./min and a faster rate may be 0.5 to 1° C./m in.

The thermal treatment may be performed in a single oven and the temperature within the oven may be decreased or increased from the first temperature to the second temperature during the treatment time. The total treatment time between the first temperature and the second temperature may be 10 to 60 min, 10 to 15 min, 10 to 20 min, 15 to 25 min, 20 to 30 min 20 to 25 min, 30 to 60 min, 40 to 60 min, 50 to 60 min, or greater than 60 min.

The temperature may be controlled by a temperature controller in an oven that controls the heating in the oven to provide the desired time versus temperature profile.

For a PDLLA/everolimus coating, the first temperature may be 45° C., 45 to 50° C., or 43 to 47° C. and the temperature is decreased to a second temperature which may be 35° C., 35 to 40° C., or 33 to 37° C. Alternatively, the first temperature may be 35° C., 35 to 40° C., or 33 to 37° C. and the temperature is increased to a second temperature which may be 45° C., 45 to 50° C., or 43 to 47° C.

In another aspect of thermally treating at a variable temperature, the temperature may vary cyclically between a first temperature and a second temperature during the treatment time. The temperature may cycle at least two times between the first temperature and the second temperature. In this way, the polymer-rich and drug-rich phases are exposed two or more times to their respective rapid aging temperatures. The temperature versus time profile may be, for example, a sinusoidal or a sawtooth waveform.

Examples—Degree of Aging and Aging Rate of Drug and Polymer

The extent and the relative rate of aging can be determined from measurements of enthalpy relaxation using differential scanning calorimetry (DSC) for the drug and polymer mixture at different temperatures. Physical aging is associated with enthalpy relaxation, therefore, when an aged sample is heated to above a glass transition temperature, it absorbs the heat it lost during its aging.

DSC provides the state of aging of a sample. In DSC experiments, an aged sample is heated from below its Tg through its Tg range at constant rate of increase in temperature. The heat re-absorbed by the sample is measured as the enthalpy of the sample. The re-absorption of heat is shown as an endothermic peak. The sample is then cooled below its Tg and heated a second time through its Tg range. The difference between the enthalpy of the second heated sample and the first heated sample is the excess enthalpy. This excess endothermic relaxation near Tg is proportional to the extent of physical aging of the material.

In the experiments described herein, samples are aged in a convection oven at a selected temperature for a selected aging time.

DSC experiments of samples of PDLLA, PDLLA/everolimus coating on metal stents, and PDLLA/everolimus coating material in a DSC pan were performed and showed the extent and the relative rate of aging of drug and polymer at different temperatures.

FIG. 4 shows the excess enthalpy versus aging time of pure PDLLA of resin samples aged at 45° C. for aging times in a range up to about one day. As shown in FIG. 4, PDLLA physical aging plateaus in about 20 min at 45° C.

FIG. 5 shows the excess aging enthalpy (normalized) versus aging time of PDLLA in a PDLLA/everolimus coating on a metal stent for aging temperatures of 35, 40, and 45° C. FIG. 5 shows that at 35° C., PDLLA ages or solidifies much faster and to a greater degree compared to 40° C. and 45° C. Therefore, PDLLA has a much faster aging rate at the lower temperature of 35° C. than the higher temperatures.

FIG. 6 shows the aging enthalpy versus aging time for everolimus in a PDLLA/everolimus coating on a metal stent at aging temperatures of 25, 30 and 40° C. FIG. 6 shows that everolimus has an opposite trend than PDLLA with faster physical aging at the higher temperature of 40° C. However, everolimus aging takes much longer time due to higher glass transition temperature at 86° C., although higher temperature still accelerates the physical aging.

Examples—Influence of Physical Aging on Crimping Damage

Singe Stage Thermal Processing

A single stage thermal processing step was performed after coating on stents having a scaffold made of a blend of PLLA and PLLA-co-CL copolymer with a coating of 50 wt % PDLLA and 50 wt % everolimus. The coated scaffold was placed in a convection oven at 45° C. for 25 min. The thermally treated coated scaffold was crimped directly without the use of a film on a balloon delivery catheter. As a control, a coated scaffold without thermal treatment was crimped over a balloon delivery catheter.

Figure 7A:
FIG. 7A depicts a PDLLA-everolimus coated scaffold without thermal treatment as pictured under an optical microscope in the crimped state.
Figure 7B:
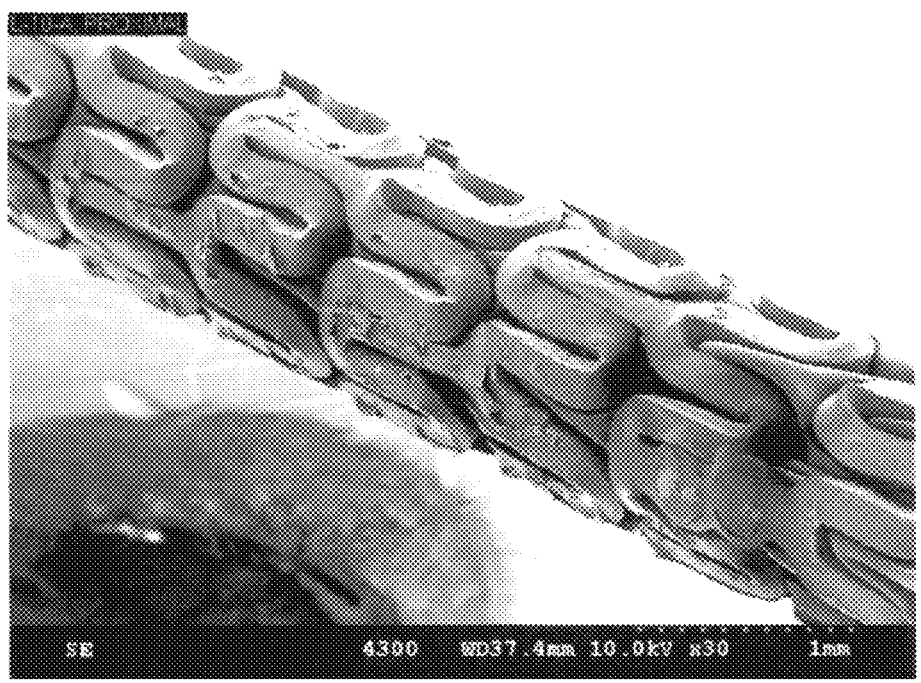
FIG. 7B depicts a PDLLA-everolimus coated scaffold without thermal treatment as pictured under scanning electron microscope (SEM) in the crimped state.

FIG. 7A depicts the PDLLA-everolimus coated scaffold without thermal treatment as pictured under an optical microscope in the crimped state and FIG. 7B depicts the coated scaffold without thermal treatment as pictured under scanning electron microscope (SEM) in the crimped state.

Figure 8A:
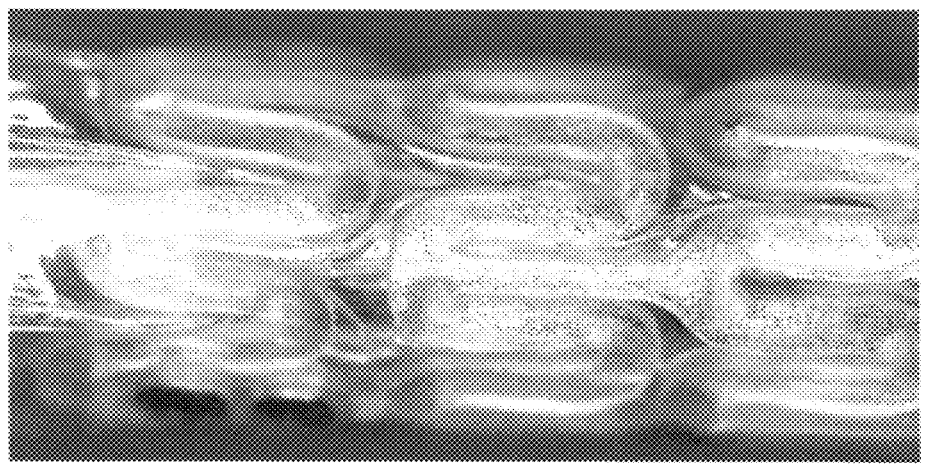
FIG. 8A depicts a PDLLA-everolimus coated scaffold with thermal treatment as pictured under an optical microscope in the crimped state.
Figure 8B:
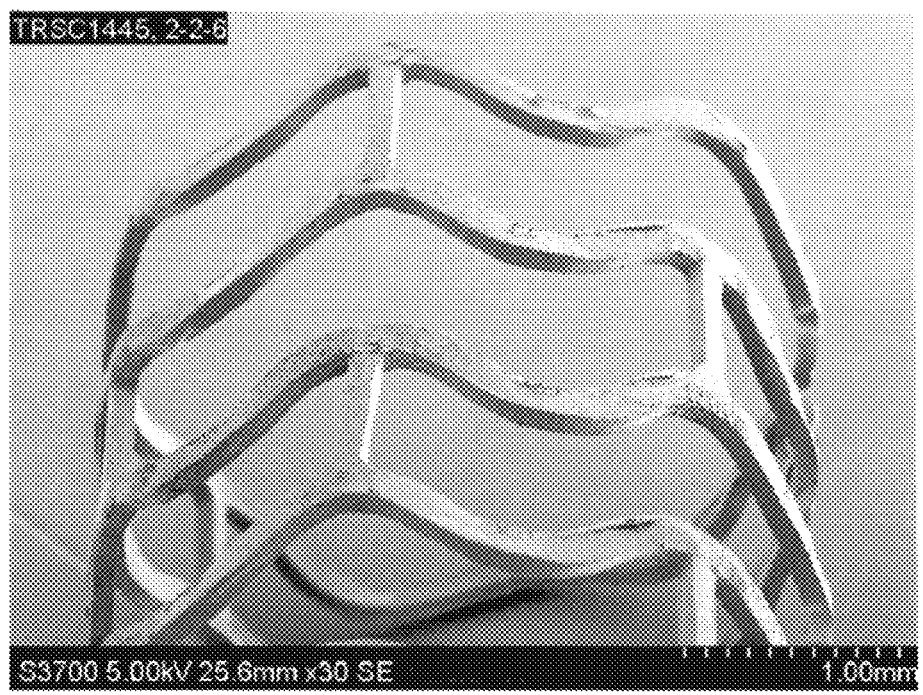
FIG. 8B depicts a PDLLA-everolimus coated scaffold with thermal treatment as pictured under SEM in the crimped state.

FIG. 8A depicts the PDLLA-everolimus coated scaffold with the thermal treatment as pictured under an optical microscope in the crimped state and FIG. 8B depicts the coated scaffold with thermal treatment as pictured under SEM in the deployed state.

A comparison of FIG. 7A with FIG. 8A and FIG. 7B with FIG. 8B demonstrates that the thermal treatment improves coating integrity during crimping process. In each instance of comparison, the tears and voids in the coating on the scaffolds without thermal treatment are not present in the coating of the scaffolds subjected to thermal treatment. The thermal treatment strengthens the scaffold coating such that it is able to maintain its integrity after being crimped and subsequently deployed as demonstrated in FIG. 8B.

Two Stage Thermal Process

The effect on crimping damage of dual or two stage physical aging thermal process on a stent coating was studied. The stents had a scaffold made of a blend of PLLA and PLLA-co-CL copolymer with a coating of 50% PDLLA and 50% everolimus. Two single stage thermal processes were also performed at different temperatures for a comparison to the two stage process.

Table 1 summarizes four studies that were performed and are labeled Group 1, 2, 3, and 4. The sample size was N≈50 for each Group. For each Group, a sample was thermally processed, followed by a pre-crimp step, and then by the final crimp step. The pre-crimp step was a partial reduction in diameter. The pre-crimp temperature was performed with heating. The pre-crimp temperature was 45° C. for Groups 1, 2, and 4 and 35° C. for Group 3. The pre-crimp outside diameter (OD) of the stent was 0.06 in for Groups 1, 2, and 4 and 0.08 in for Group 3. The final crimped outside diameter of the scaffold was 0.0345 in for all groups.

TABLE 1

Studies of thermal processing of PDLLA/everolimus coated scaffolds.

| Group | Description | 1st Oven | $2^{nd}$ Oven | Pre-Crimp Process | N |
|---|---|---|---|---|---|
| 1 | Control | 45° C./1 hr (Use 6 batch system) | N/A | Nominal (Crimp to 0.06 inch OD at 45° C.) | 55 |
| 2 | 2 ovens | 45° C./25 min | 35° C./50 min | Nominal | 50 |
| 3 | 2 ovens + Pre-crimp | 45° C./25 min | 35° C./50 min | Crimp to 0.08 inch OD at 35° C. | 68 |
| 4 | Low Temp | 40° C./1 hr | 40° C./1 hr | Nominal | 48 |

An on-line inspection of each sample after pre-crimp and crimp was performed for each sample for the presence of coating defects, such as peels (i.e., lifted flaps of coating), tears, and voids. The defects were divided into minor and major categories based on the size of the defect. Minor defects were defined as ≤0.02 mm$^2$ in size, while major defects were defined as >0.02 mm$^2$ in size. Units categorized as having minor defects could not have any major defects.

As shown in Table 1, Groups 1 and 4 are single stage thermal processes in a single oven with Group 1 treated at 45° C. and Group 4 treated at 40° C. Groups 2 and 3 are both two stage processes with the first stage at 45° C. (25 min) in one oven and the second stage in a second oven at 35° C. (50 min). Table 2 depicts the results of an on-line inspection and re-inspection of minor and major defects at pre-crimp and final crimp.

TABLE 2

Inspection of crimping damage of thermally treated coated scaffolds.

| | | Pre-Crimp Damage (%) | | | Final Damage (%) | | |
|---|---|---|---|---|---|---|---|
| Group | Sample size - N | Minor | Major (online) | Major (reinspect) | Minor | Major (online) | Major (reinspect) |
| Group 1 | 55 | 36.36 | 10.91 | 3.64 | 34.55 | 9.09 | 5.45 |
| Group 2 | 50 | 42 | 18 | 0 | 52 | 0 | 0 |
| Group 3 | 68 | 14.71 | 1.47 | 1.47 | 36.76 | 2.94 | 2.94 |
| Group 4 | 48 | 35.42 | 6.25 | 6.25 | 45.83 | 4.17 | 6.25 |

With regard to the on-line inspection, there appears to be no clear trend of reduction in damage at pre-crimp operation and no clear trend in reduction in damage for the minor category for both the pre-crimp or final crimp. The trends for major damage at final for Groups 2, 3 and 4 are less damage than the Group 1 control.

With regard to re-inspection, Group 2 pre-crimp samples were borderline but acceptable which confirms the pre-crimp to final discrepancy from online data. The reduction in the presence of major defects from the on-line inspection to the reinspection for Group 2 may be attributed to some of the lifted coating induced at the pre-crimp operation being pressed down by the final crimp process. Groups 1 and 4 at final re-inspection are closer than on-line inspection. The re-inspection at final was the same as the online inspection for groups 2 and 3.

Coating Formation

A polymer coating over a scaffold may be formed using various solution techniques which involve application of a coating composition including a polymer, drug, and solvent to the scaffold surface, followed by removing the solvent. The coating composition can be applied to a scaffold substrate by various methods, such as, dip coating, brushing, or spraying. The aspects of the present invention are not limited to any particular application or deposition technique. In particular, spray coating a stent typically involves mounting or disposing a stent on a support, followed by spraying a coating composition from a nozzle onto the mounted stent. Solvent is removed from the deposited coating composition to form the coating. There typically is some residual solvent remaining in the coating after the solvent removal or solvent removal steps. As discussed in more detail below, solvent removal can be performed through evaporation at room or ambient temperature or by heating or exposing a coated stent to a temperature above room temperature.

If a coating layer of a target thickness (or mass) is formed with a single application step and then followed by solvent removal, the coating layer that results can be nonuniform, include coating defects, or both. Stents, particularly those for coronary use, comprise an intricate stent pattern with small dimensions. When too much coating applied all at once to load the desired amount of drug, the applied solution could form webs, pools, or strands in the stent pattern. Instead of the desired conformal coating, a highly nonuniform coating results. Therefore, a coating of a target thickness (or mass) is preferably formed with two or more cycles or passes of a coating composition application, such as spraying. After each cycle or pass, a solvent removal or drying step is performed. The solvent removal step after each pass is referred to as interpass drying. A cycle or pass refers to the application of a coating composition without an intervening solvent removal step, such as blowing warm air on the stent. In spraying, a cycle or pass can include directing the spray plume over the length of a stent one or more times. After each coating composition application pass, the application of coating composition on the substrate is stopped, which is followed by interpass solvent removal. An exemplary coating process is described in US 2010/0323093.

Exemplary solvents used in the solution processing methods include acetone, chloroform, methyl ethyl ketone (MEK), and cyclohexanone combined with acetone.

The thickness of the therapeutic coating layer may be 1 to 5 microns, or more narrowly, 1 to 2 microns, 2 to 3 microns, 3 to 5 microns, 4 to 5 microns or greater than 5 microns.

The therapeutic coating layer may be applied on all surfaces of the scaffold, the abluminal or outer surface, luminal or inner surface, and sidewall surfaces. In some aspects, therapeutic coating layer may be applied exclusively on selected surfaces, for the abluminal surface, luminal surface, or both.

Additionally, the thickness of a layer or layers on a particular surface may not be uniform across the surface. Also, the thickness or average thickness for the abluminal surface, luminal surface, and sidewall surface may be different.

After each pass of applying a coating composition during the coating process, the coating may be subjected to a drying step that includes heating the stent to a temperature above ambient to remove solvent. The temperature may, for example, be 40 to 50° C. or greater than 40° C. and less than a Tg of the coating polymer.

After the final pass in forming the therapeutic layer, the coating may include residual solvent. The coating may or may not be subjected to a further solvent removal step that includes heating the scaffold, such as baking in an oven, at a mild temperature for a suitable duration of time (e.g., 30 min to 4 hr) or by the application of warm air. The mild temperature may be less than the Tg of the coating polymer. For a polylactide scaffold polymer the solvent removal temperature may be 40 to 50 deg C.

At the completion of forming the therapeutic coating, the coating may have less than 5 wt % residual solvent, or more narrowly, 0.1 to 1 wt %, 1 to 5 wt %, 1 to 2 wt %, or 2 to 3 wt %.

Scaffold Formation and Materials

A biodegradable stent may be fabricated from a tube with a thin wall initially having no holes or voids. The pattern of structural elements may be formed by laser machining the tube. Material is removed by cutting out selected regions of the tube which results in the pattern of structural elements.

The manufacturing process for a bioabsorbable stent may include several steps. A polymeric tube may be formed using melt processing such as extrusion or injection molding. Prior to laser machining, the tube may be processed to modify its mechanical properties that also improves stent properties such as radial strength and resistance to fracture. Such processes may include radially deforming the tube. The scaffold pattern may then be formed by laser machining. A therapeutic coating may be formed over the scaffold.

A radially expandable scaffold or stent body should have the ability to hold open narrowed portions of blood vessels. Therefore, the scaffold should possess a radial strength in an expanded state that is sufficiently high and sustainable to maintain the expanded vessel size for a period of weeks or months. A polymer or polymer formulation for a scaffold should be stiff and strong after processing into a scaffold under physiological conditions within a human body. Polymer or polymer formulations that have a glass transition temperature (Tg) in a dry state sufficiently above human body temperature (approximately 37 deg C.), particularly those that include semicrystalline polymers, meet the above criterial. Polylactide and polylactide based polymers such as poly(L-lactide) (PLLA) are examples of such polymers.

The polymer or polymer formulation of a scaffold may include polylactide-based polymers such as, but are not limited to poly(L-lactide) (PLLA), poly(D,L-lactide), poly(L-lactide-co-caprolactone) (PLLA-co-CL), poly(L-lactide-co-glycolide) (PLGA), or poly(DL-lactide-co-glycolide). The copolymers may be random or block copolymers. The poly(DL-lactide) homopolymer or copolymer component of a polymer formulation can have a constitutional unit weight percentage L-lactide and D-lactide units of 50/50 to 96/4, such as 50/50 or 96/4 poly(DL-lactide). The term "unit" or "constitutional unit" refers to the composition of a monomer as it appears in a polymer. The PLLA-co-CL copolymer can have a weight or mole percentage of caprolactone units of 1 to 10% or more narrowly 1 to 5%, 5 to 10%, 1 to 3%, 3 to 5%, 5 to 8%, or 8 to 10%. PLGA copolymer can have molar percentages of L-lactide or DL-lactide and glycolide units, of 90:10, 75:25, 50:50, 25:75, and 10:90.

The polymer or polymer formulation of a scaffold may further include a blend of a PLA polymer with PCL homopolymer; a blend of a PLA homopolymer and a PLA-co-PCL copolymer; and a blend of a PCL homopolymer and a PLA and PCL copolymer. A homopolymer refers to a polymer that is composed of only one type of constitutional unit with only trace amounts of other types of units, for example, less than 1 mol % or 0.01 mol %.

A scaffold may be made of a blend of a PLA homopolymer and a PLA-co-PCL copolymer in which the PLA homopolymer is PLLA or PDLLA. The PLA-co-PCL copolymer may be PLLA-co-CL or PDLLA-co CL. The PLA-co-PCL copolymer may be 1 to 20 wt %, 1 to 15 wt %, 5 to 20 wt %, 5 to 15 wt %, 10 to 20 wt %, 15%, 12 to 18 wt %, or 10 to 15 wt % of the blend. The PLA homopolymer may be 80 to 99 wt %, 85 to 99 wt %, 80 to 95 wt %, 85 to 95 wt %, 80 to 90 wt %, 85 wt %, 82 to 88 wt %, or 85 to 90 wt % of the blend. The caprolactone units in the PLA-co-PCL copolymer may be 1 to 10% (wt % or mol %) of the blend, or more narrowly, 1 to 3%, 3 to 5%, 5 to 10%, 2 to 8%, or 3 to 8% of the blend. The random copolymer may be 1% to 50% caprolactone units. Exemplary random copolymers include 95/5 PLA-co-PCL and 70/30 PLA-co-PCL, wherein, for example, 95/5 refers to 95 mol % lactide and 5 mol % caprolactone.

The scaffold may be made substantially or completely of the polymer formulation. "Substantially" may correspondent to greater than 90 wt %, greater than 95 wt %, or greater than 99 wt %. The scaffold may have a composition of 90 to 95% or 95 to 99% of the polymer formulation.

The scaffold or the polymer formulation of the scaffold may have a degree of crystallinity of less than 5%, 5 to 20%, 20 to 55%, 20 to 30%, 30 to 40%, 40 to 45%, 45 to 40%, or 50 to 55%. In other embodiments, the scaffold or the polymer formulation of the scaffold may be amorphous or substantially amorphous.

Drugs or Therapeutic Agents

The drug in the aspects of the present invention includes an antiproliferative, anti-inflammatory or immune modulating, anti-migratory, anti-thrombotic or other pro-healing agent or a combination thereof. The anti-proliferative agent can be a natural proteineous agent such as a cytotoxin or a synthetic molecule or other substances such as actinomycin D, or derivatives and analogs thereof (manufactured by Sigma-Aldrich 1001 West Saint Paul Avenue, Milwaukee, Wis. 53233; or COSMEGEN available from Merck) (synonyms of actinomycin D include dactinomycin, actinomycin IV, actinomycin I1, actinomycin X1, and actinomycin C1), all taxoids such as taxols, docetaxel, and paclitaxel, paclitaxel derivatives, all olimus drugs such as macrolide antibiotics, rapamycin, everolimus, novolimus, myolimus, deforolimus, umirolimus, biolimus, merilimus, temsirolimus structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Representative rapamycin derivatives include 40-O-(3-hydroxy)propyl-rapamycin, 40-O-[2-(2-hydroxy)ethoxy]ethyl-rapamycin, or 40-O-tetrazole-rapamycin, 40-epi-(N1-tetrazolyl)-rapamycin (ABT-578 manufactured by Abbott Laboratories, Abbott Park, Ill.), prodrugs thereof, co-drugs thereof, and combinations thereof.

The anti-inflammatory agent can be a steroidal anti-inflammatory agent, a nonsteroidal anti-inflammatory agent, or a combination thereof. In some embodiments, anti-inflammatory drugs include, but are not limited to, novolimus, myolimus, alclofenac, alclometasone dipropionate, algestone acetonide, alpha amylase, amcinafal, amcinafide, amfenac sodium, am iprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, mom iflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof.

These agents can also have anti-proliferative and/or anti-inflammatory properties or can have other properties such as antineoplastic, antiplatelet, anti-coagulant, anti-fibrin, anti-thrombotic, antimitotic, antibiotic, antiallergic, antioxidant as well as cystostatic agents. Other active agents which are currently available or that may be developed in the future are equally applicable.

Definitions

Room or ambient temperature may be 25° C., 20 to 30° C., 20 to 25° C., 25 to 30° C., or any temperature or range between 20 and 30° C.

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is increased, the heat capacity increases. The increasing heat capacity corresponds to an increase in heat dissipation through movement. Tg of a given polymer can be dependent on the heating rate and can be influenced by the thermal history of the polymer as well as its degree of crystallinity. Furthermore, the chemical structure of the polymer heavily influences the glass transition by affecting mobility. The Tg can be determined as the approximate midpoint of a temperature range over which the glass transition takes place. [ASTM D883-90]. The most frequently used definition of Tg uses the energy release on heating in differential scanning calorimetry (DSC). As used herein, the Tg refers to a glass transition temperature as measured by differential scanning calorimetry (DSC) at a 20° C./min heating rate. Unless stated otherwise, values for "Tg" refer to an upper limit for Tg (E.g., for poly(L-lactide) and the Tg when the material is dry. Poly(L-lactide) has a glass transition temperature range of between about 55 to 60 Deg. C. "Tg" for poly(L-lactide), for purposes of this disclosure, Tg is 60 Deg. C), or up to 65 Deg. C. for a strain hardened tube. The glass transition temperature is a function of chain flexibility. The glass transition occurs when there is enough vibrational (thermal) energy in the system to create sufficient free-volume to permit sequences of 6-10 main-chain carbons to move together as a unit. At this point, the mechanical behavior of the polymer changes from rigid and brittle to tough and leathery.

The "melting temperature" (Tm) is the temperature at which a material changes from solid to liquid state. In polymers, Tm is the peak temperature at which a semicrystalline phase melts into an amorphous state. Such a melting process usually takes place within a relatively narrow range (<20° C.), thus it is acceptable to report Tm as a single value.

"Modulus" may be defined as the ratio of a component of stress or force per unit area applied to a material divided by the strain along an axis of applied force that result from the applied force. For example, a material has both a tensile and a compressive modulus.

"Hardness" is a measure of how resistant solid matter is to various kinds of permanent shape change when a compressive force is applied. Hardness measurements include scratch, indentation (e.g., nanoindentation), and rebound.

"Toughness", or "fracture toughness" is the amount of energy absorbed prior to fracture, or equivalently, the amount of work required to fracture a material. One measure of toughness is the area under a stress-strain curve from zero strain to the strain at fracture. The stress is proportional to the tensile force on the material and the strain is proportional to its length. The area under the curve then is proportional to the integral of the force over the distance the polymer stretches before breaking. This integral is the work (energy) required to break the sample. The toughness is a measure of the energy a sample can absorb before it breaks. There is a difference between toughness and strength. A material that is strong, but not tough is said to be brittle. Brittle materials are strong, but cannot deform very much before breaking.

The "degree of crystallinity" may be expressed in terms of, $w_c$ (mass fraction), $\varphi_c$ (volume fraction) and refers to mass fraction or volume fraction of crystalline phase in a sample of polymer. The mass-fraction and the volume-fraction degrees of crystallinity are related by the equation, $w_c = \varphi_c \rho/\rho_c$, where $\rho$ and $\rho_c$ are the mass concentrations (mass densities) of the entire sample and of the crystalline phase, respectively. The degree of crystallinity can be determined by several experimental techniques. Among the most commonly used are: (i) x-ray diffraction, (ii) calorimetry (DSC), (iii) mass density measurements, (iv) infrared spectroscopy (IR), (v) solid-state NMR spectroscopy, and (vi) vapor permeability. Unless stated otherwise, throughout this description a degree of crystallinity given for a polymer is expressed as a percentage (%) of crystallinity and expressed as a mass or volume fraction. Unless stated otherwise throughout this description a degree of crystallinity given for a polymer composition is expressed as a percentage (%) of crystallinity and expressed as a mass fraction.

Measurements of crystallinity may also be determined from a modified method of differential scanning calorimetry (DSC), e.g., over a temperature range of 30 Deg. C. to 150 Deg. C, with modulation amplitude of 0.5° C. and heat rate of 6° C./minute and duration of 1 minute.

"Amorphous" or "substantially amorphous" means no greater than, or less than 5% crystallinity, or not more than 1%, 2% or 4% crystallinity.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

What is claimed is:

1. A method of fabricating a stent comprising:
   providing a stent including a scaffold and a coating over the scaffold, wherein the coating comprises a polylactide-based polymer mixed with a drug, and wherein the coating includes drug-rich domains and a polymer-rich phase;
   thermally treating the coating at a first temperature followed by thermally treating the coating at a second temperature different than first temperature, wherein the first and second temperatures are less than glass transition temperatures (Tg's) of the drug and the polymer and the first temperature is greater than the second temperature, wherein an aging rate of the drug at the first temperature is greater than at the second temperature and an aging rate of the polymer at the second temperature is greater than the aging rate of the polymer at the first temperature; and
   crimping the stent after the thermal treatments from a fabricated diameter to a reduced diameter for delivery into a vascular lumen, wherein the thermal treatments reduce crimping damage to the coating.

2. The method of claim 1, wherein the thermal treatments increase a strength and modulus of the coating.

3. The method of claim 1, wherein the polymer is poly (DL-lactide) and the second temperature is 30 to 35° C.

4. The method of claim 3, wherein a time of the thermal treatment at the second temperature is 10 to 15 min.

5. The method of claim 1, wherein the drug is everolimus or sirolimus and the first temperature is 40 to 50° C.

6. The method of claim 5, wherein a time of the thermal treatment at the second temperature is 20 to 30 min.

7. A method of fabricating a stent comprising:
   providing a stent including a scaffold and a coating over the scaffold, wherein the coating comprises a polylactide-based polymer mixed with a drug;
   thermally treating the coating at a temperature that varies during a thermal treatment time, wherein the temperature starts at a first temperature and decreases to a second temperature during the thermal treatment, the first temperature is less than a glass transition temperature (Tg) for the drug, the second temperature is less than the glass transition temperatures (Tg's) for the drug and for the polymer and the first temperature is greater than the second temperature, wherein an aging rate of the drug at the first temperature is greater than at the second temperature and an aging rate of the polymer at the second temperature is greater than the aging rate of the polymer at the first temperature; and
   crimping the stent after the thermal treatments from a fabricated diameter to a reduced diameter for delivery into a vascular lumen, wherein the thermal treatments reduce crimping damage to the coating.

8. The method of claim 7, wherein the temperature decreases linearly between the first temperature and the second temperature.

9. The method of claim 7, wherein the thermal treatment is performed in a single oven and the temperature within the oven decreases between the first temperature to the second temperature during the treatment time.

10. The method of claim 7, wherein the thermal treatments increase a strength and modulus of the coating.

11. The method of claim 7, wherein the polymer is poly(DL-lactide) and the second temperature is 30 to 35° C.

12. The method of claim 7, wherein the drug is everolimus or sirolimus and the first temperature is 40 to 50° C.

13. The method of claim 7, wherein a time of the thermal treatment is 20 to 60 min.

* * * * *